United States Patent
Wortman et al.

[11] Patent Number: 6,131,469
[45] Date of Patent: Oct. 17, 2000

[54] SHEAR FORCE MEASUREMENT DEVICE FOR BEDS AND METHOD

[75] Inventors: Ronald D. Wortman, Angola; Michael P. Rechin, Silver Creek; Charles P. Stahl, Hamburg, all of N.Y.

[73] Assignee: Gaymar Industries, Inc., Orchard Park, N.Y.

[21] Appl. No.: 09/336,469

[22] Filed: Jun. 18, 1999

[51] Int. Cl.[7] .............................. G01N 3/22; G01B 7/16
[52] U.S. Cl. ................................................ 73/841; 73/770
[58] Field of Search .......................... 73/770, 763, 769, 73/841, 7

[56] References Cited

U.S. PATENT DOCUMENTS

| | | | |
|---|---|---|---|
| 4,140,008 | 2/1979 | Golemebeck et al. .................. 73/78 |
| 4,669,302 | 6/1987 | Wagner et al. ......................... 73/172 |
| 4,794,935 | 1/1989 | Viesturs .................................. 600/587 |
| 5,148,706 | 9/1992 | Masuda et al. ......................... 73/172 |

*Primary Examiner*—Max Noori
*Attorney, Agent, or Firm*—Hodgson Russ Andrews Woods & Goodyear LLP

[57] ABSTRACT

The present invention is a device to measure the parallel shear force on a mattress. The device has a motor, a weighted object, a high friction material pad, and a load cell. The motor moves by pushing and pulling the weighted object on the high friction material pad which is on the mattress. The load cell measures the peak shear force when the weighted object is pulled and when the weighted object is pushed.

16 Claims, 2 Drawing Sheets

6,131,469

SHEAR FORCE MEASUREMENT DEVICE FOR BEDS AND METHOD

FIELD OF THE INVENTION

The present invention generally relates to devices and methods for measuring shear forces applied to beds.

BACKGROUND OF THE INVENTION

Until recently, the only way to evaluate the effectiveness of a support surface was by measuring the tissue interface pressure (TIP). TIP is a vertical force exerted when soft tissue is compressed over the bony prominence that causes capillary closure. This closure can result in ischemia, and subsequent cell death. Pressure, however, is only one part of the pressure-ulcer equation. Another important factor in the development of pressure-ulcers is shear. Shear is a parallel force that occurs when the skin and underlying subcutaneous tissue are pulled taut and over-stretched, causing tissue deformity, obstructing blood flow, and necrosis.

Research has shown that pressure-ulcers are a result of a pressure/shear relationship. (Bennet L. et al. Shear vs. Pressure as Causative Factors in Skin Blood Flow Occlusion. Arch. Phys. Med. Rehab. 1979; 60:309–314) An inverse relationship exits between pressure and shear. The greater the shear, the less pressure required to cause tissue damage. According to the research, the critical ratio is 2:1, which means that it takes twice as much shear force to equal pressure, (1 mmgHg of pressure≈2 units of shear. This ratio between vertical pressure and parallel shear force is called, by Gaymar Industries, Inc., the Isolibrium Factor.

A problem with evaluating the Isolibrium Factor was that it was difficult to accurately and effectively measure. The present invention solves this problem.

SUMMARY OF THE INVENTION

The present invention is a device to measure the parallel shear force on a mattress. The device has a motor, a weighted object, a high friction material pad, and a load cell. The motor moves by pushing and pulling the weighted object on the high friction material pad which is on the mattress. The load cell measures the peak shear force when the weighted object is pulled and when the weighted object is pushed.

BRIEF DESCRIPTION OF THE DRAWINGS

For a further understanding of the invention, as well as its characterizing features, reference should now be made to the accompanying drawings wherein.

DETAILED DESCRIPTION OF THE PRESENT INVENTION

It is an object of the present invention to provide a device and method for measuring the shear force of a mattress unit in a uniform manner.

Figure 1:
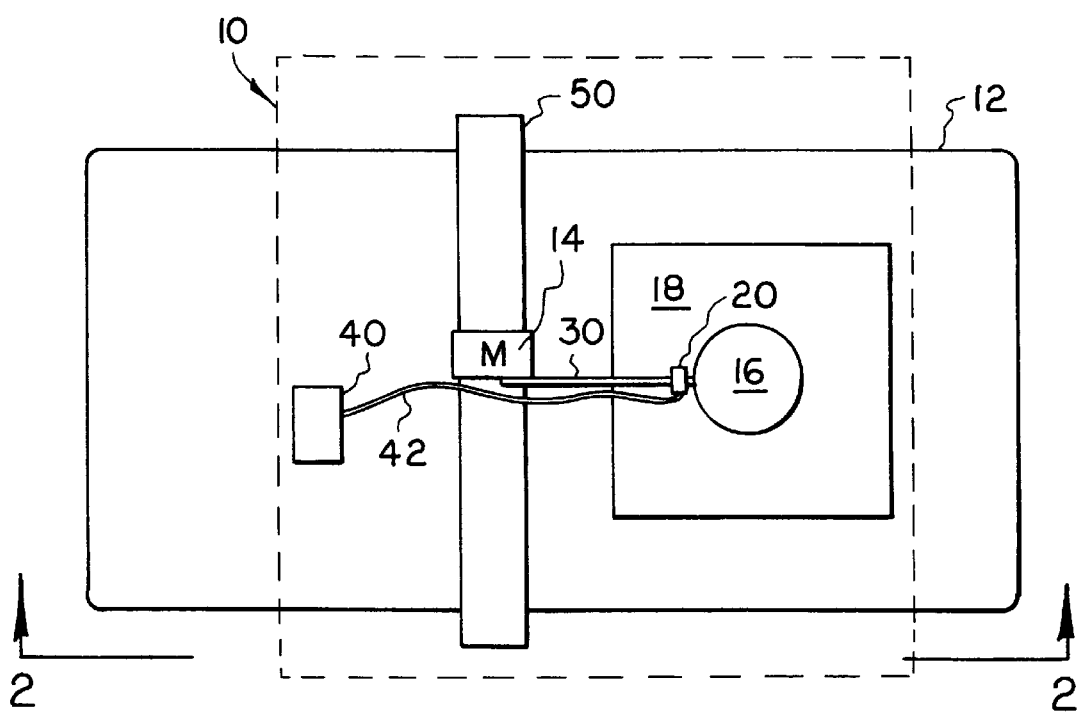
FIG. 1 is a top view of the present invention.

FIG. 1 shows a top plan view of a shear force measuring device 10 for a mattress 12. The device 10 has a motor 14, a weighted object 16, a high friction material pad 18, and a load cell 20.

The motor 14 is any conventional motor having a drive that provides a predetermined stroke. In particular, the motor 10 is a small electric motor, to decrease exhaust, with a 1.6 RPM with an eccentric drive to provide a ⅜ stroke. This motor 14 moves, at a predetermined distance, the weighted object 16.

Figure 2:
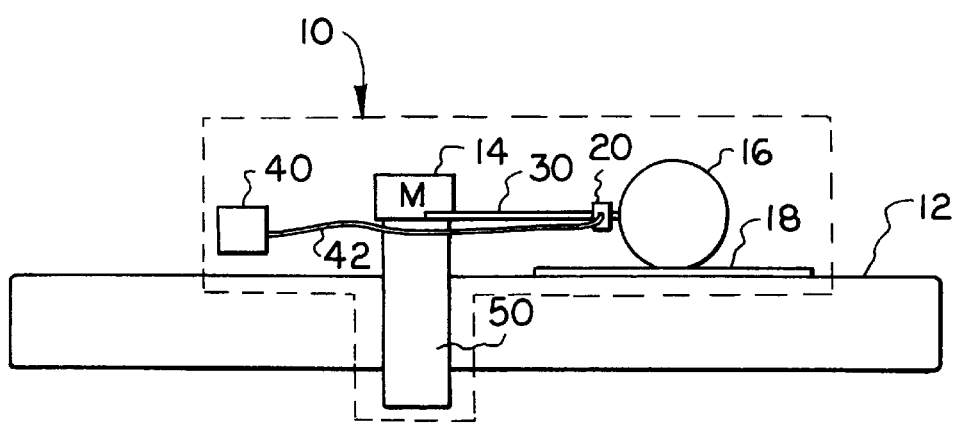
FIG. 2 is a side view of the present invention taken along lines 2—2 of FIG. 1.
Figure 4:
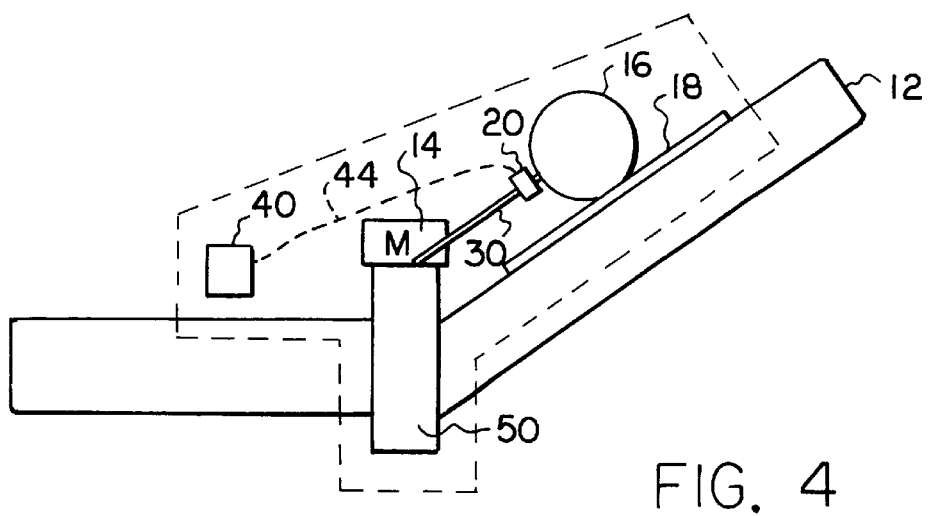
FIG. 4 is an alternative embodiment of FIG. 2.

The weighted object 16 is a bowling ball or any other object which can represent a bony structure of a patient. The object 16 moves a predetermined distance because the object 16 is interconnected to the drive of the motor 14 through a rod 30. As shown in FIGS. 2 and 4, the rod 30 is, preferably, parallel to the plane of the mattress 12 where the measurement is being taken.

The measurement is taken when the object 16 is pushed along the high friction material pad 18 and when the object 16 is pulled along the high friction material pad 18. The distance of the push and pull movements are a predetermined distance which is equal to the stroke of the motor 14.

The high friction material pad 18 is conventional material that minimizes the movement of a patient on a mattress 12. This pad is commonly referred to in the mattress industry as a "skootguard." The pad 18 is used to represent human skin upon the mattress 12. The pad 18 is placed on the mattress 12.

The mattress 12 can be a flat mattress, as shown in FIG. 2, or an adjustable mattress as shown in FIG. 4. In either case, the mattress 12 is the mattress itself, or the mattress with various layers thereon. The various layers can include a blanket, flame blocker material, a sheet, another skootguard, polyethylene inserts, zipped covers, unzipped covers, and combinations thereof.

In particular, the blankets can be wool, cotton, a polymeric material, an electric blanket, a hypo/hyperthermia blanket or combinations thereof. The sheets can also be wool, cotton, polymeric material, or combinations thereof.

Figure 3:
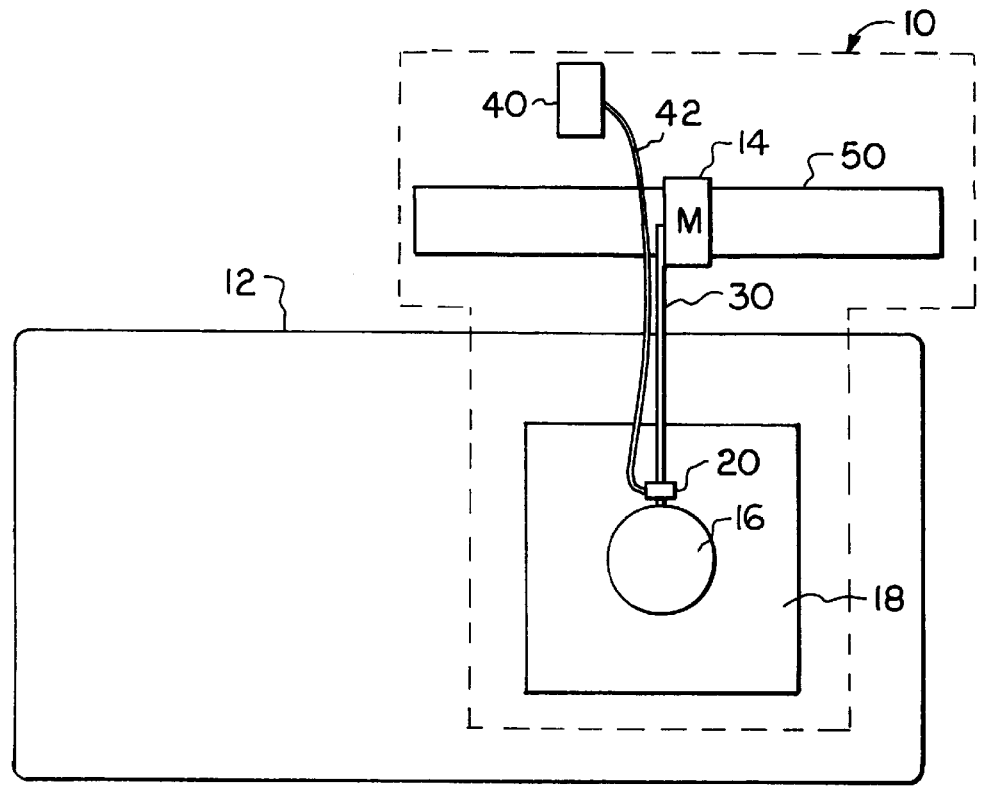
FIG. 3 is an alternative embodiment of FIG. 1.

The load cell 20 measures the peak shear force when the weighted object is pulled and when the weighted object is pushed upon the pad 18. An example of a conventional load cell is a low profile tension link (model LC703) by New. The load cell 20 measures the shear force and transmits the measurement to a read-out device 40. The load cell 20 may transmit the measurement to the read-out 40 through an interconnected cable 42, as illustrated in FIGS. 1–3, or by transmitting a signal 44.

The read-out device 40 can be hand-held device, a personal computer, or any other device that can display and/or record the measurement of shear force for evaluative purposes.

Alternatively, the motor 14 is mounted on a stabilizing apparatus 50. Apparatus 50 ensures that when the motor 14 is operating only the weighted object 16 and rod 30 move. The apparatus 50 can be positioned anywhere in relation to the mattress 12, as shown in FIGS. 1 and 3. The apparatus 50 must also have a certain height above the mattress 12 in order for the rod 30 to be essentially parallel to the plane of the mattress 12 which is to be measured. Obviously, any portion of the mattress 12 can be measured with device 10.

By accurately measuring the shear force of a mattress 12, the device 10 allows hospitals and individuals to select a bed surface that is flexible and loose to reduce shear forces, which in turn prevents pressure ulcers.

The interconnections between the rod 30 and weighted object 16, rod 30 and motor 14, motor 14 and apparatus 50, load cell 20 and weighted object 16, and load cell 20 and cable 42 are all conventional interconnections. Examples of conventional interconnections include, and not limited to, screws, bolts, threaded apertures, adhesives, crimped, hook and loop fasteners, and buckle and latch systems.

Although a preferred embodiment of the invention has been disclosed in detail for illustrative purposes, it will be recognized that there are variations of modifications of the preferred embodiment, including the rearrangement of parts, which lie within the scope of the present invention.

We claim:

1. A device to measure the parallel shear force on a mattress, the device comprising a motor, a weighted object, a high friction material pad positioned on the mattress, and a load cell;

the motor pushes and pulls the weighted object a predetermined distance along a plane parallel to the mattress and on the high friction material pad; and the load cell measures the peak shear force when the weighted object is pulled and when the weighted object is pushed.

2. The device of claim 1 further comprising a read-out device.

3. The device of claim 2 wherein the load cell transmits the measurement to the read-out device.

4. The device of claim 1 wherein the weighted object is a bowling ball.

5. The device of claim 1 further comprising a rod interconnecting the motor to the weighted object.

6. The device of claim 1 wherein the mattress is an adjustable mattress.

7. The device of claim 1 wherein the mattress is a flat mattress.

8. The device of claim 1 further comprising a rod interconnecting the weighted object and motor, wherein the rod is essentially parallel to the plane of the area of the mattress which is being measured.

9. A method to measure the parallel shear force on a mattress, comprising the steps of:

operating a device comprising a motor, a weighted object, a high friction material pad positioned on the mattress, and a load cell wherein the motor pushes and pulls the weighted object a predetermined distance along a plane parallel to the mattress and on the high friction material pad; and measuring the peak shear force with a load cell when the weighted object is pulled and when the weighted object is pushed.

10. The method of claim 9 further comprising a read-out device.

11. The method of claim 10 wherein the load cell transmits the measurement to the read-out device.

12. The method of claim 9 wherein the weighted object is a bowling ball.

13. The method of claim 9 further comprising a rod interconnecting the motor to the weighted object.

14. The method of claim 9 wherein the mattress is an adjustable mattress.

15. The method of claim 9 wherein the mattress is a flat mattress.

16. The method of claim 9 further comprising a rod interconnecting the weighted object and motor, wherein the rod is essentially parallel to the plane of the area of the mattress which is being measured.

* * * * *